(12) United States Patent
Sasayama et al.

(10) Patent No.: US 8,986,274 B2
(45) Date of Patent: Mar. 24, 2015

(54) ABSORBENT ARTICLE HAVING JOINT REGIONS

(75) Inventors: Kenichi Sasayama, Kagawa (JP); Hirotomo Mukai, Kagawa (JP); Tomoko Tsuji, Kagawa (JP); Tatsuya Hashimoto, Kagawa (JP); Shinji Noma, Kagawa (JP); Kei Wakasugi, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 900 days.

(21) Appl. No.: 11/951,803

(22) Filed: Dec. 6, 2007

(65) Prior Publication Data

US 2008/0140038 A1 Jun. 12, 2008

(30) Foreign Application Priority Data

Dec. 8, 2006 (JP) ................. 2006-331241

(51) Int. Cl.
*A61F 13/496* (2006.01)
*A61F 13/72* (2006.01)
*A61F 13/15* (2006.01)

(52) U.S. Cl.
CPC ....... *A61F 13/15739* (2013.01); *A61F 13/4963* (2013.01); *A61F 13/496* (2013.01)
USPC ............... 604/385.11; 604/396; 428/196

(58) Field of Classification Search
CPC ........... A61F 13/15739; A61F 13/4963; A61F 13/538
USPC ............... 604/385.11, 395, 396; 428/196
See application file for complete search history.

(56) References Cited

U.S. PATENT DOCUMENTS

| | | | | |
|---|---|---|---|---|
| 2,705,687 A | * | 4/1955 | Petterson et al. | 428/198 |
| 3,009,822 A | * | 11/1961 | Griswold et al. | 428/195.1 |
| 3,087,833 A | * | 4/1963 | Drelich | 428/198 |
| 3,802,817 A | * | 4/1974 | Matsuki et al. | 425/66 |
| 3,949,128 A | * | 4/1976 | Ostermeier | 428/152 |
| 4,188,436 A | * | 2/1980 | Ellis et al. | 428/198 |

(Continued)

FOREIGN PATENT DOCUMENTS

| | | |
|---|---|---|
| GB | 1332037 | * 10/1973 |
| JP | 7227407 | 8/1995 |

(Continued)

OTHER PUBLICATIONS

Machine translation of Japanese Patent Application Publication No. 2002-272785 to Suzuki et al., Sep. 24, 2002.*

(Continued)

*Primary Examiner* — Melanie Hand
*Assistant Examiner* — Paula L Craig
(74) *Attorney, Agent, or Firm* — Morrison & Foerster LLP

(57) ABSTRACT

The present invention provides an absorbent article in which a joining strength between sheet-shaped members is improved. A joint portion which joins a front trunk-surrounding region and a rear trunk-surrounding region of the absorbent article to each other has a first joint region arranged continuously along an outer edge and the second joint portion arranged continuously in a region closer to the outer edge than the first joint region, substantially parallel to the first joint region. The sum of the areas of the plurality of first joint portions in the first joint region is less than the sum of the areas of the second joint portions in the second joint region.

3 Claims, 5 Drawing Sheets

(56) References Cited

U.S. PATENT DOCUMENTS

| | | | | |
|---|---|---|---|---|
| 4,663,220 | A | * | 5/1987 | Wisneski et al. ............. 428/221 |
| 4,938,817 | A | * | 7/1990 | Langley ....................... 156/73.1 |
| 5,074,854 | A | * | 12/1991 | Davis ....................... 604/385.11 |
| 5,163,932 | A | * | 11/1992 | Nomura et al. ........... 604/385.29 |
| 5,292,239 | A | * | 3/1994 | Zeldin et al. .................... 425/66 |
| 5,618,366 | A | * | 4/1997 | Suekane ..................... 156/73.1 |
| 5,624,420 | A | * | 4/1997 | Bridges et al. ................. 604/365 |
| 5,626,574 | A | * | 5/1997 | Sasaki et al. ............. 604/385.29 |
| 5,685,874 | A | * | 11/1997 | Buell et al. .................... 604/396 |
| 5,931,827 | A | * | 8/1999 | Buell et al. ............... 604/385.29 |
| 5,948,710 | A | * | 9/1999 | Pomplun et al. ............. 442/341 |
| 6,508,797 | B1 | * | 1/2003 | Pozniak et al. .......... 604/385.11 |
| 6,537,935 | B1 | * | 3/2003 | Seth et al. ..................... 442/366 |
| 6,620,490 | B1 | * | 9/2003 | Malchow et al. ............. 428/196 |
| 6,713,159 | B1 | | 3/2004 | Blenke et al. |
| 2002/0022114 | A1 | * | 2/2002 | Sorensen et al. ............. 428/190 |
| 2002/0032427 | A1 | * | 3/2002 | Schmitz et al. .......... 604/385.11 |
| 2003/0059587 | A1 | * | 3/2003 | Grimm et al. ................ 428/196 |
| 2006/0089616 | A1 | * | 4/2006 | Belau et al. ................... 604/389 |
| 2007/0073261 | A1 | * | 3/2007 | Ashton et al. ................. 604/389 |
| 2009/0292266 | A1 | * | 11/2009 | Back ............................. 604/365 |
| 2012/0278975 | A1 | * | 11/2012 | Yamashita et al. ................ 2/400 |

FOREIGN PATENT DOCUMENTS

| | | |
|---|---|---|
| JP | H08511709 | 12/1996 |
| JP | 9-287 | 5/1997 |
| JP | 2002272785 | 9/2002 |
| JP | 2003-24382 | 1/2003 |
| JP | 2004520961 | 7/2004 |
| JP | 2004-267335 | 9/2004 |
| JP | 2007135940 | 6/2007 |

OTHER PUBLICATIONS

Human translation of JP 2002-272785 to Suzuki et al., Sep. 24, 2002.*

Notice of Reasons for Rejection dated Mar. 5, 2013, directed to Japanese Application No. 2008-548339; 5 pages.

* cited by examiner

ABSORBENT ARTICLE HAVING JOINT REGIONS

This application is based on and claims the benefit of priority from Japanese Patent Application No. 2006-331241, filed on 8 Dec. 2006, the content of which is incorporated herein by reference.

BACKGROUND OF THE INVENTION

1. Field of the Invention

The present invention relates to an absorbent article.

2. Related Art

Examples of conventional absorbent articles that absorb excreta emanated from the bodies include sanitary napkins, disposable diapers, and training pants. The absorbent articles, which are appropriately used depending on lifestyles, care levels, or the like of wearers, include liquid-permeable surface sheets, liquid-impermeable back sheets, and absorbent bodies arranged between the surface sheets and the back sheets, and are so adapted that the absorbent bodies keep the emanated excreta such as urine through the surface sheets and the back sheets prevent the excreta from leaking out of the absorbent articles at the time of wearing.

Furthermore, disposable diapers of various types such as unfolded types and pants types have been proposed in accordance with the intended uses. The pants-type disposable diaper, for example, is formed in the shape of pants having a trunk opening and a pair of leg openings by previously joining a front trunk-surrounding region and a rear trunk-surrounding region to each other at both their side edges with heat sealing or the like when used. Such pants-type disposable diapers are widely employed by babies to adult incontinent persons.

In the pants-type disposable diaper, it is required that the front trunk-surrounding region and the rear trunk-surrounding region are firmly joined to each other during use and can be easily peeled after use in joint portions at the side edges. However, in recent years, sheet-shaped members having low basis weights may be used from the viewpoint of low cost and reduced environmental load, and sheet-shaped members with specialized stretchability, textures, or the like to improve value of disposable diapers may be used. Such sheet-shaped members reduce the durable strength of joint portions.

Generally, the durable strength of the joint portions has a property of being greatly affected by the basis weights of sheet-shaped members to be joined to each other and the types thereof and their combinations. However, the lower the basis weight of the sheet-shaped members becomes, the lower the durable strength of the joint portions becomes. In order to use sheet-shaped members having a low basis weight, the sheet-shaped members must be, therefore, joined to each other with such a joint pattern that the durable strength of the joint portions can be efficiently increased.

On the other hand, Japanese Unexamined Patent Application, First Publication No. 07-227407 (hereinafter referred to as Patent Document 1), for example, discloses a disposable diaper in which sheet-shaped members are joined to each other by a plurality of transverse adhesive lines and at least one longitudinal adhesive line that are discontinuously arranged in one row or two rows in a longitudinal direction.

In the disposable diaper disclosed in Patent Document 1, a sheet laminate including an absorbent body is folded into front and rear portions, and both their respective right and left side portions are joined to each other along the side edges thereof, to form joint portions. The joint portions are composed of a plurality of transverse adhesive lines and at least one longitudinal adhesive line that are formed by way of heat sealing. The transverse adhesive lines are discontinuously arranged in one row or two rows in a longitudinal direction, and the at least one longitudinal adhesive line is provided so as to come into contact with or intersect at least one of the transverse adhesive lines.

In a case where the at least one longitudinal adhesive line is provided closer to an outer edge of the joint portion, for example, in the disposable diaper disclosed in Patent Document 1, when a load is applied to a joint portion facing a transverse force, perpendicular to the longitudinal direction, to attempt to peel a joint region, the longitudinal adhesive line facing the transverse force is in contact with the transverse adhesive lines. In the disposable diaper disclosed in Patent Document 1, the joint part facing the transverse force is thus dispersed. Therefore, the joining strength cannot be sufficiently increased even if the bonding area is increased.

On the other hand, in a case where the at least one longitudinal adhesive line is provided at an inner end of the joint portion in the disposable diaper, for example, a sufficient strength is exhibited for the transverse force. However, the adhesive line itself functions as an inductive line for cutting in the longitudinal direction of the joint portion. When a force is applied in the longitudinal direction, for example, when a wearer pulls up the disposable diaper at the time of wearing, the joint portion may be torn with little force.

SUMMARY OF THE INVENTION

The present invention has been made in view of the foregoing problem, and has an objective to provide an absorbent article in which a joining strength between sheet-shaped members is improved.

In order to attain the abovementioned object, the inventors of the present invention have discovered that a joining strength between joint portions in an absorbent article is improved even when sheet-shaped members having a low basis weight or sheet-shaped members with specialized stretchability, texture, or the like, for example, are used by joining the joint portions to each other in a predetermined pattern, to complete the present invention. Specifically, an objective of the present invention is to provide the following disposable diaper.

In a first aspect of the present invention an absorbent article includes a plurality of sheets composing a chassis having at least a front trunk-surrounding region and a rear trunk-surrounding region arranged therein, having a width direction and a longitudinal direction perpendicular to the width direction, and at least a first joint region closer to the inside of the chassis and a second joint region closer to the outside of the chassis in a joint region where the front trunk-surrounding region and the rear trunk-surrounding region are joined to each other along both side edges thereof, in which a plurality of first joint portions are continuously formed in the longitudinal direction in the first joint region, a plurality of second joint portions are continuously formed in the longitudinal direction in the second joint region, and the sum of the areas of the plurality of first joint portions in the first joint region is less than the sum of the areas of the second joint portions in the second joint region.

In a second aspect of the absorbent article as described in the first aspect of the present invention, the distance between respective arrays in the width direction of the first joint portions and the second joint portions is in the range of zero to 1.5 mm.

In a third aspect of the absorbent article as described in the first or second aspect of the present invention, a first distance in a predetermined direction between the adjacent first joint portions of the plurality of first joint portions is greater than a second distance in the predetermined direction between the adjacent second joint portions of the plurality of second joint portions.

In a fourth aspect of the absorbent article as described in any one of the first to third aspects of the present invention, the plurality of sheets include one or a plurality of non-woven fabrics, in which fibers composing the non-woven fabric in the joint regions are oriented so as to connect at least the first joint portion and the second joint portion in close proximity to each other.

In a fifth aspect of the absorbent article as described in any one of the first to fourth aspects of the present invention, the joint region is a joint region where the front trunk-surrounding region and the rear trunk-surrounding region are joined to each other along both side edges thereof, and includes a first joint region closer to the inside of the chassis and a second joint region closer to the outside of the chassis, and further includes a third joint region arranged closer to the outside of the chassis than the second joint region, in which the third joint region has a plurality of third joint portions continuously formed therein in the longitudinal direction, and the sum of the areas of the plurality of third joint portions in the third joint region is less than the sum of the areas of the second joint portions in the second joint region.

Here, each of the joint regions is a region between lines connecting both ends, in the width direction perpendicular to a predetermined direction, of each of the joint portions in the predetermined direction.

The present invention can provide an absorbent article in which a joining strength between sheet-shaped members is improved.

DETAILED DESCRIPTION OF THE INVENTION

Embodiments of the present invention are described with reference to the drawings. The present embodiment is not limited to the following embodiment, and the technical scope of the present invention is not limited to the same. Although in the present embodiment of the present invention, a description is provided of a pants-type disposable diaper, for example, the present invention is not limited to the same. For example, the embodiment of the present invention may be used for joint portions in a sanitary napkin that has for an object of absorbing menstrual blood excreted from the opening of the vagina of a female. That is, the embodiment of the present invention may provide an absorbent article including an absorbent body having liquid holding properties and a plurality of sheets arranged such that at least parts at their outer edges are laminated.

1. Embodiment 1-1. Overall Configuration

The overall configuration of a disposable diaper 1 according to an embodiment of the present invention is described. It should be noted that a surface, directed toward the body of a wearer, of the disposable diaper 1 is considered to be a skin contacting surface, and a surface on the opposite side of the skin contacting surface is considered to be a skin non-contacting surface.

Figure 1:
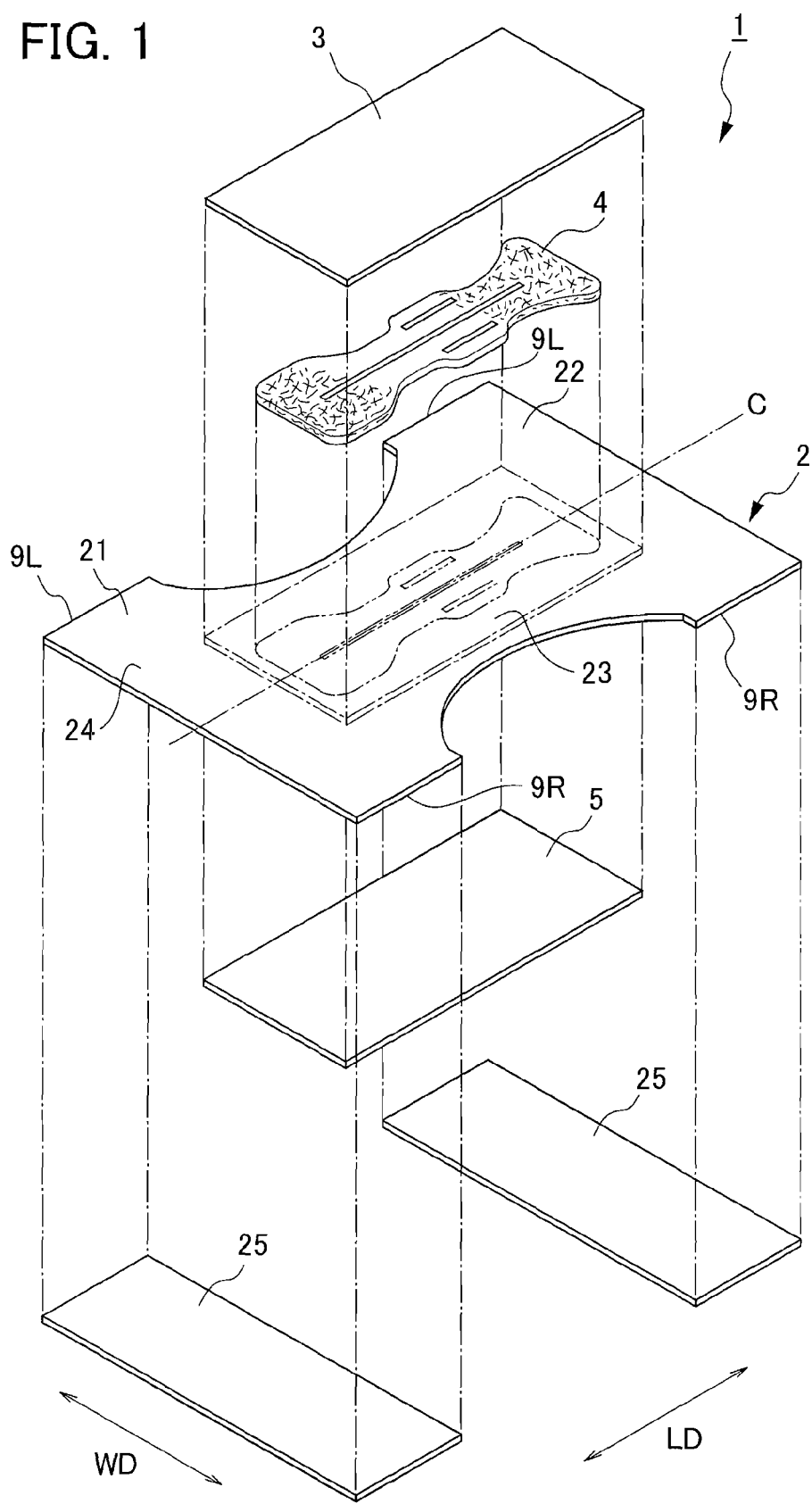
FIG. 1 is a perspective exploded view showing an unfolded state of a pants-type disposable diaper according to an embodiment of the present invention.
Figure 2:
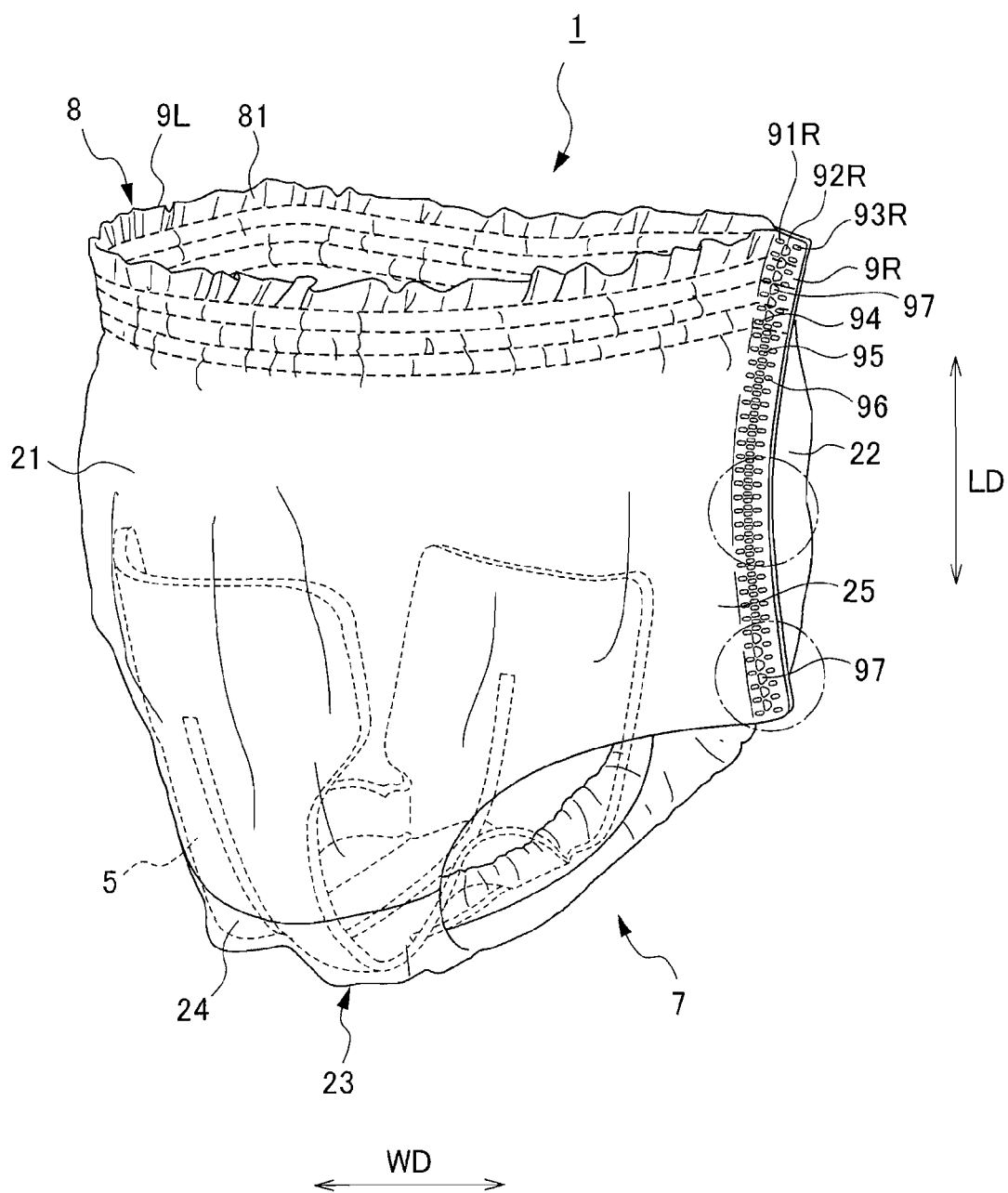
FIG. 2 is a diagram showing the pants-type disposable diaper according to the embodiment of the present invention.

As shown in FIGS. 1 and 2, the disposable diaper 1 serving as an absorbent article includes a chassis 2 forming the outer shape of the disposable diaper 1 and formed in the shape of pants at the time of wearing; a liquid-permeable surface sheet 3 provided on a surface, on the side of the skin contacting surface, of the chassis 2 and formed in a substantially vertically-long shape composing a top surface layer; a liquid-impermeable back sheet 5 provided on a surface, on the side of the non-skin contacting surface, of the chassis 2 and formed in a substantially vertically-long shape composing a back surface layer; and an absorbent body 4 having liquid holding properties arranged between the surface sheet 3 and the chassis 2 and formed in a substantially vertically-long shape composing an absorbing layer.

The surface sheet 3 is arranged on the side of the body and is brought into contact with an excretory portion of a wearer when employed. The surface sheet 3 may be liquid-permeable throughout or may be partially liquid-impermeable. Furthermore, the surface sheet 3 may be composed of one sheet-shaped member or may be formed by bonding a plurality of sheet-shaped members to one another.

The absorbent body 4 has liquid holding properties and is formed in a substantially vertically-long shape Here, "substantially vertically-long shape" shall include a substantially rectangular shape having a longitudinal direction LD and a width (shorter-side) direction WD, and shall further include a shape having both sides in the longitudinal direction LD partially recessed in a direction toward the center in the longitudinal direction LD and a shape that is raised in the opposite direction to the direction toward the center. That is, it is assumed that a portion in the longitudinal direction LD of the absorbent body 4 differs in length in the width direction WD.

The absorbent body 4 may be wrapped in a tissue (not shown) or a hydrophilic non-woven fabric (not shown). When wrapped in the hydrophilic non-woven fabric, the absorbent body 4 may not use the surface sheet 3 or may only partially use the surface sheet 3. This allows the production cost to be reduced, for example.

One may have a non-woven fabric or the like joined to its surface on the side of the non-skin contacting surface used as the back sheet 5. It is preferable that a non-woven fabric or the like is thus joined to the surface, on the side of the non-skin contacting surface, of the back sheet 5 because the feel at the time of wearing by the wearer, for example, is improved. Furthermore, when a film is used for the back sheet 5, it is preferable that a non-woven fabric or the like is joined to the film because an uncomfortable sound can be prevented from being produced due to friction of the film, for example. Although the back sheet 5 is arranged on the non-skin contacting surface in the present embodiment, the present invention is not limited to the same. For example, the back sheet 5 may be provided between the absorbent body 4 and the chassis 2. Alternatively, when the chassis 2 is formed of a plurality of sheet-shaped members, the back sheet 5 may be provided between the sheet-shaped members.

The chassis 2 has a front trunk-surrounding region 21, a rear trunk-surrounding region 22, and an under-crotch region 23 formed between the front trunk-surrounding region 21 and the rear trunk-surrounding region 22 at the time of wearing. Furthermore, used as the chassis 2 is a so-called composite sheet mainly composed of a sheet 24 forming the outer shape of the disposable diaper 1 and sheets 25 affixed to the front trunk-surrounding region 21 and the rear trunk-surrounding region 22 of the chassis 2, respectively. The composite sheet is a sheet-shaped member obtained by laminating (joining) a stretchable non-woven fabric and a non-stretchable non-woven fabric. An example of the sheet 24 serving as a non-stretchable non-woven fabric is a sheet-shaped member serving as a spunbonded non-woven fabric composed of polypropylene fibers and having a basis weight of 19 $g/m^2$. Furthermore, an example of the sheet 25 serving as a stretchable non-woven fabric is a sheet-shaped member serving as a spunbonded non-woven fabric composed of combined filament yarn fibers of polypropylene and polyurethane and having a basis weight in polypropylene of 22 $g/m^2$ and a basis weight in polyurethane of 13 $g/m^2$.

Furthermore, the sheet 25 is affixed and joined to the sheet 24, as described above, by hot melting, thermal welding, ultrasonic welding, or the like with the sheet 25 expanded by 2.0 times in the width direction WD of the disposable diaper 1 and contracted by 0.65 times in the longitudinal direction LD of the disposable diaper 1. Thus, the chassis 2 has predetermined stretchability by affixing the sheet 24 and the sheet 25.

In the disposable diaper 1, a thread-shaped elastic member 81 may be arranged in a region surrounding a trunk opening 8 in order to make the trunk opening 8 elastic. Thus, the disposable diaper 1 has trunk-surrounding gathers formed therein. Furthermore, in the disposable diaper 1, a thread-shaped elastic member (not shown) may be arranged in a region surrounding a leg opening 7 in order to make the leg opening 7 elastic. Thus, the disposable diaper 1 has leg gathers formed therein.

1-2. Joint Region of Chassis 2

As shown in FIG. 2, the disposable diaper 1 is formed in the shape of so-called pants by joining the front trunk-surrounding region 21 and the rear trunk-surrounding region 22 of the chassis 2 to each other in a predetermined joint pattern in joint regions 9L and 9R formed in portions, at both side edges (outer edges) in a trunk surrounding direction of the front trunk-surrounding region 21 and the rear trunk-surrounding region 22, laminated so as to be overlapped with each other and formed in a substantially vertically-long shape. Thus, the trunk opening 8 positioned around the abdomen of the wearer in a wearing state and the pair of leg openings 7 respectively positioned around the legs of the wearer are formed in the disposable diaper 1. Here, the total basis weight of a compatible component in a joint portion is 40 $g/m^2$ to 90 $g/m^2$.

The joint pattern in the joint regions 9L and 9R of the disposable diaper 1 are described next. It should be noted that the joint region 9L has the same configuration as the joint region 9R, which is hidden in the figure. The joint regions 9L and 9R are provided with first joint regions 91L and 91R, second joint regions 92L and 92R, and third joint regions 93L and 93R, respectively, that extend in the longitudinal direction LD of the disposable diaper 1, are parallel in the width direction WD, and are formed in a substantially vertically-long shape. The first joint regions 91L and 91R, the second joint regions 92L and 92R, and the third joint regions 93L and 93R are regions for convenience in distinguishing respective arrays of joint portions 94, 95, and 96 described later, and are continuous regions including the joint portions arranged in the longitudinal direction at a predetermined interval. Specifically, the first joint regions 91L and 91R are arranged inside the disposable diaper 1 in the joint regions 9L and 9R, respectively, i.e. closer to the inside of the chassis 2, closer to a center line C (see FIG. 1) for dividing the disposable diaper 1 into two in the width direction WD. The third joint regions 93L and 93R are arranged outside the disposable diaper 1 in the joint regions 9L and 9R, respectively, i.e. closer to a side edge in the width direction WD of the disposable diaper 1. The second joint regions 92L and 92R are arranged between the first joint regions 91L and 91R and the third regions 93L and 93R, respectively. In other words, the second joint regions 92L and 92R are respectively arranged closer to the outside of the chassis 2 than the first joint regions 91L and 91R, and the third joint regions 93L and 93R are respectively arranged closer to the outside of the chassis 2 than the second joint regions 92L and 92R.

Although in the present embodiment, the first joint regions 91L and 91R, the second joint regions 92L and 92R, and the third joint regions 93L and 93R are provided in the joint regions 9L and 9R, respectively, the present invention is not limited to the same. For example, only the first joint regions 91L and 91R and the second joint regions 92L and 92R may be provided.

Each of the first joint regions 91L and 91R has a plurality of first joint portions 94 provided by ultrasonically sealing the front trunk-surrounding region 21 and the rear trunk-surrounding region 22 of the chassis 2, provided therein in at least one row in the longitudinal direction LD of the first joint region. Each of the second joint regions 92L and 92R has a plurality of second joint portions 95 provided by ultrasonically sealing the front trunk-surrounding region 21 and the rear trunk-surrounding region 22 of the chassis 2, provided therein in at least one row in the longitudinal direction LD of the second joint region. Furthermore, each of the third joint regions 93L and 93R has a plurality of third joint portions 96 provided by ultrasonically sealing the front trunk-surrounding region 21 and the rear trunk-surrounding region 22 of the chassis 2, provided therein in at least one row in the longitudinal direction LD if the third joint region. Although in the present embodiment, the front trunk-surrounding region 21 and the rear trunk-surrounding region 22 of the chassis 2 are joined to each other using ultrasonic sealing, the present invention is not limited to the same. For example, the front trunk-surrounding region 21 and the rear trunk-surrounding region 22 may be joined to each other using heat sealing.

Here, it is preferable that a distance j in the width direction WD between the respective arrays of the first joint portion 94 in the first joint region 91L or 91R and the second joint portion 95 in the second joint region 92L or 92R is between 0 and 1.5 mm. It is not preferable for the distance j to be not more than zero because the disposable diaper 1 is liable to be continuously break in the longitudinal direction LD (so-called straight cut). It is not preferable for the distance j to be more than 1.5 mm because a joining strength may not, in some cases, be improved even when the first joint regions 91L and 91R and the second joint regions 92L and 92R, respectively, cooperate with each other. Furthermore, a distance k in the width direction WD between the second joint portion 95 in the second joint region 92L or 92R and the third joint portion 96 in the third joint regions 93L or 93R can be made similar to the distance j.

Figure 3A:
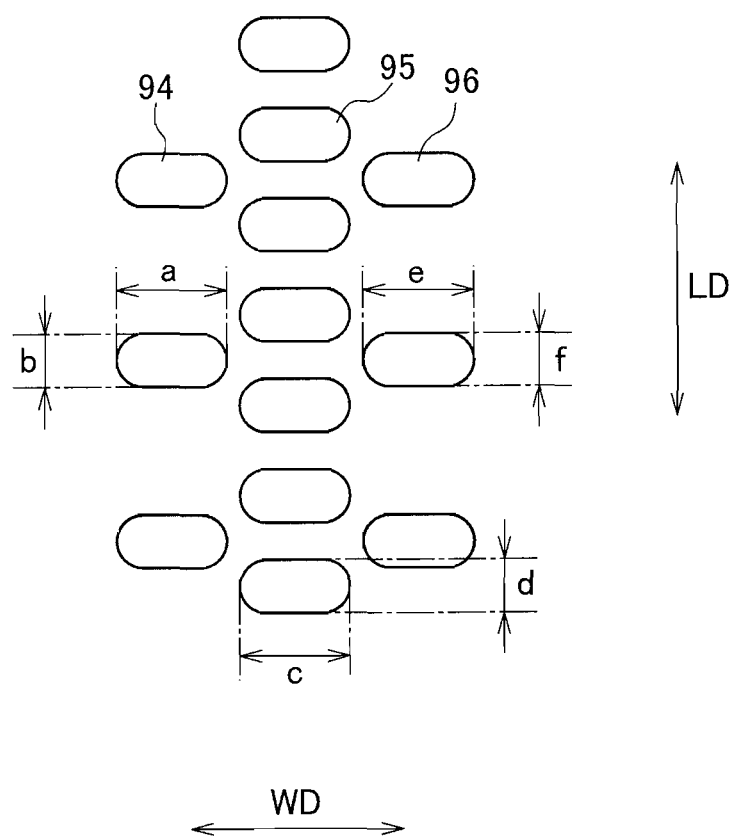
FIG. 3A is a diagram showing a joint pattern in a joint portion of the disposable diaper according to the present invention.
Figure 3B:
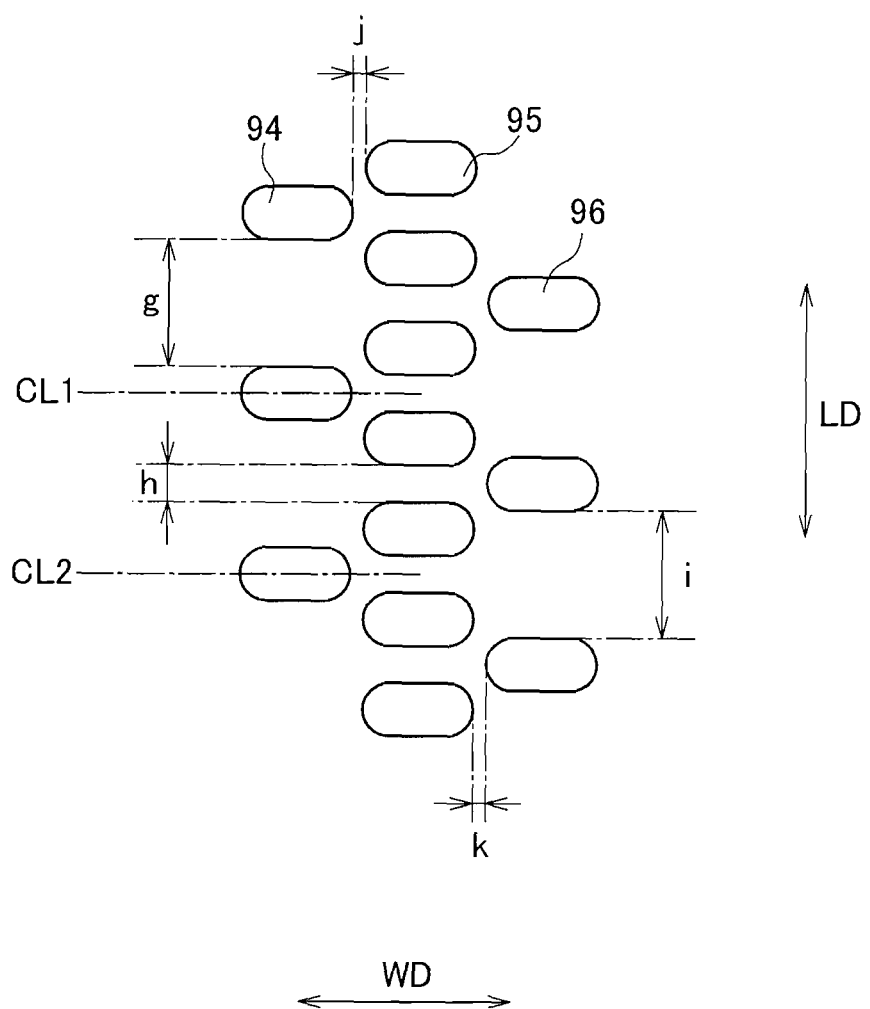
FIG. 3B is a diagram showing a joint pattern in a joint portion of the disposable diaper according to the present invention.

The first joint portions 94, the second joint portions 95, and the third joint portions 96 are respectively arranged in predetermined patterns in the first joint region 91L or 91R, the second joint region 92L or 92R, and the third joint region 93L or 93R. The sum of the areas of the plurality of first joint portions 94 is less than the sum of the areas of the plurality of second joint portions 95. Furthermore, the first joint portions 94 are spaced a predetermined distance apart such that the first joint portions 94 are at least one less in number than the second joint portions 95 in the longitudinal direction LD (in the longitudinal direction LD of the disposable diaper 1), as shown in FIGS. 3A and 3B.

It should be noted that the predetermined distance is a distance for equally spacing the first joint portions 94 apart at positions corresponding to positions between the adjacent second joint portions 95 in the first joint region 91L or 91R, for example. In other words, the first joint portions 94 are arranged abeam in the width direction of the gap between the second joint portions 25 (non-joint portion), and arranged at a longer interval than that of the neighboring second joint portions 25. Specifically, the first joint portions 94 and the second joint portions 95 can be formed such that the two joint portions 95 are arranged between a center line CL1 for equally dividing the first joint portion 94 in the longitudinal direction LD and a center line CL2 for equally dividing the first joint portion 94, which is adjacent thereto in the longitudinal direction LD, in the longitudinal direction LD.

With the array of the second joint portions 95 made more densely spaced than the array of the first joint portions 94, and the first joint portion 94 and the second joint portion 95 arranged such that their positions in the width direction WD of the disposable diaper 1 are not overlapped with each other, even when a force in the longitudinal direction LD of the disposable diaper 1 to tear the joint portions is exerted, for example, a durable strength for the longitudinal direction of the joint portions (the longitudinal direction LD of the disposable diaper 1) can be thus improved because the first joint portions 94 and the second joint portions 95 are alternately arranged, respectively, with different pitches.

When the total area of the second joint portions 95 in the second joint region 92L or 92R is greater than the total area of the first joint portions 94 in the first joint regions 91L or 91R, the necessity of arranging the first joint portions 94 and the second joint portions 95 with the two joint portions 95 between the center lines CL1 and CL2, as described above, is eliminated. For example, the first joint portions 94 and the second joint portions 95 may be arranged in a one-to-one relationship. In this case, a strength durable in the longitudinal direction (the longitudinal direction LD of the disposable diaper 1) can be also improved by making the array of the first joint portions 94 and the array of the second joint portions 95 different from each other and arranging the arrays substantially parallel to each other such that the positions of the first joint portion 94 and the second joint portion 95 in the width direction WD of the disposable diaper 1 are not overlapping with each other. Furthermore, even when a force in the width direction WD of the disposable diaper 1 to peel the chassis 2 is exerted, a joining strength for peeling (a force in the width direction WD of the disposable diaper 1) can be also improved because the area ratio of the second joint portions 95 in the second joint region 92L or 92R is greater than the area ratio of the first joint portions 94 in the first joint region 91L or 91R.

Figure 5:
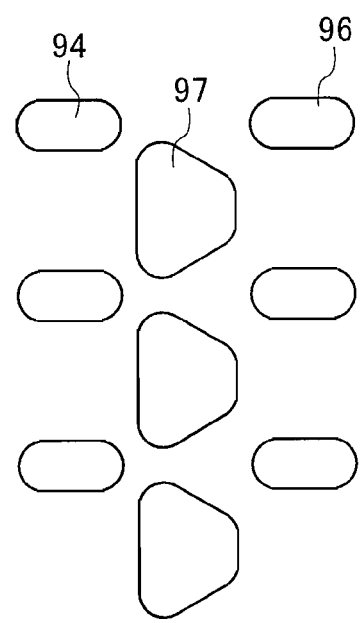
FIG. 5 is a diagram showing a joint pattern in a joint portion of the disposable diaper according to the present invention.

As shown in FIGS. 2 and 5, second joint portions 97 having a greater junction area than the second joint portions 95 are provided in portions on the side of the trunk opening and the leg openings, respectively, of the second joint region 92L or 92R. The second joint portion 97 is formed in a shape as shown in FIG. 5, for example. The second joint portions 97 are, therefore, having a greater junction area than the second joint portions 95 prevents the disposable diaper 1 from being completely broken because the plurality of second joint portions 97 having a great junction area are provided even if the first joint portions 94 are peeled upon application of a force in such a direction as to peel the disposable diaper 1 in the joint regions 9L and 9R that are respectively overlapped. That is, a joining strength for the peeling caused by pulling is improved.

The third joint regions 93L and 93R are respectively arranged at positions opposed to the first joint regions 91L and 91R with the second joint regions 92L and 92R interposed therebetween. That is, the third joint regions 93L and 93R are respectively arranged closer to the side edges of the disposable diaper 1. The third joint portions 96 provided in the third joint region 93L or 93R can use a joint pattern having the same shape as the first joint portions 94. Alternatively, the third joint portions 96 may use a joint pattern having a different shape from the first joint portions 94. That is, the third joint portions 96 feel softer by having a greater non-joint region than the second joint region 92L or 92R. Even if the second joint portions 95 are peeled, the third joint portions 96 can prevent the disposable diaper 1 from being broken.

The third joint portions 96 have the same shape and size as those of the first joint portions 94, and are spaced a first distance apart in the third joint region 93L or 93R. The third joint portions 96 may be respectively arranged at the same positions as (parallel to) the first joint portions 94 in the longitudinal direction LD, as shown in FIG. 3A, or may be alternated with the first joint portions 94 in the longitudinal direction LD, as shown in FIG. 3.

1-2-2. Shape of Joint Portion

As shown in FIG. 3A, each of the first joint portion 94, the second joint portion 95, and the third joint portion 96 is formed in the shape of a substantially laterally-long ellipse (a rounded rectangle) so as to extend in the width direction WD of the disposable diaper 1. An example of the first joint portion 94 is one having a size a in the longer-side direction (a length in the width direction WD of the disposable diaper 1) of 1.8 mm and having a size b in the shorter-side direction (a length in the longitudinal direction LD of the disposable diaper 1) of 1.0 mm. For example, the size a in the longer-side direction of the first joint portion 94 may be in a range from 0.5 mm to 5.0 mm, and the size b in the shorter-side direction may be in a range of 0.5 mm to 5.0 mm.

An example of the second joint portion 95 is one having a size c in the longer-side direction (a length in the width direction WD of the disposable diaper 1) of 1.8 mm and having a size d in the shorter-side direction (a length in the longitudinal direction LD of the disposable diaper 1) of 1.0 mm. For example, the size c in the longer-side direction of the second joint portion 95 may be in a range of 0.5 mm to 10.0 mm, and the size d in the shorter-side direction may be in a range of 0.5 mm to 5.0 mm.

An example of the third joint portion 96 is one having a size e in the longer-side direction (a length in the width direction WD of the disposable diaper 1) of 1.8 mm and having a size f in the shorter-side direction (a length in the longitudinal direction LD of the disposable diaper 1) of 1.0 mm. For example, the size e in the longer-side direction of the third joint portion 96 may be in a range of 0.5 mm to 10.0 mm, and the size f in the shorter-side direction may be in a range of 0.5 mm to 5.0 mm. It should be noted that the third joint portion 96 can have the same shape and size as those of the first joint portion 94.

Figure 4:
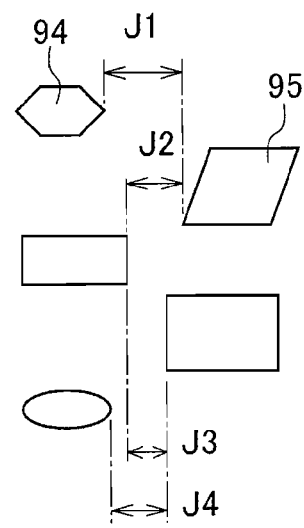
FIG. 4 is a diagram showing another form of the joint pattern.

Although in the present embodiment each of the first joint portion 94, the second joint portion 95, and the third joint portion 96 may have the shape of a substantially laterally-long ellipse, the present invention is not limited to the same. For example, it can have various shapes such as a polygon, a circle, an ellipse, and a polygon having corners that are rounded, as shown in FIG. 4.

1-2-3. Distance Between Joint Portions

As shown in FIG. 3B, the first joint portions 94, the second joint portions 95, and the third joint portions 96 are equally spaced predetermined distances apart, respectively, in the longitudinal direction LD and the width direction WD of the disposable diaper 1. For example, a distance g serving as a first distance between the first joint portions 94 (a distance in the longitudinal direction LD of the disposable diaper 1) is 2.6 mm. It should be noted that the distance g between the first joint portions 94 may be in a range of 1.5 mm to 10.0 mm and longer than the size b in the shorter-side direction of the first joint portion 94.

A distance h serving as a second distance between the second joint portions 95 (a distance in the longitudinal direction LD of the disposable diaper 1) is 0.8 mm. It should be noted that the second joint portions 95 may be arranged such that the distance h between the second joint portions 95 is in a range of 0.8 mm to 10.0 mm, and the total area of the second joint portions 95 in the second joint region 92L or 92R is greater than the total area of the first joint portions 94 in the first joint region 91L or 91R. Furthermore, exemplified as a distance i serving as a third distance between the third joint portions 96 can be a distance in the same distance range as the distance g between the first joint portions 94.

A distance j between the first joint portion 94 and the second joint portion 95 is 0.55 mm. Exemplified as the distance j between the first joint portion 94 and the second joint portion 95 can be a distance of more than 0.0 mm and not more than 1.5 mm. Exemplified as a distance k between the second joint portion 95 and the third joint portion 96 can be 0.55 mm. Exemplified as the distance j between the first joint portion 94 and the second joint portion 95 can be a distance of more than 0.0 mm and not more than 1.5 mm. That is, exemplified as the distance between the adjacent joint portions can be a distance of more than 0.0 mm and not more than 1.5 mm.

It should be noted that the distance j between the first joint portion 94 and the second joint portion 95 is in a direction extending substantially parallel to the width direction WD of the disposable diaper 1. When the first joint portion 94 is in the shape of a polygon and the second joint portion 95 is in the shape of a polygon such as a parallelogram, for example, as shown in FIG. 4, distances j1, j2, j3, and j4 in a direction parallel to the width direction WD of the disposable diaper 1 between their respective vertexes may be in the abovementioned range.

Here, the junction area of the joint portions and the distance therebetween can be adjusted depending on the position in the joint region 9L or 9R. As shown in FIG. 2, the junction area of the second joint portions 97 formed on the side of the trunk opening 8 and on the side of the leg openings 7, respectively, in the joint region 9L or 9R can be increased. That is, the second joint region 92L or 92R has predetermined regions where the second joint portions 97 greater than the second joint portions 95 are continuously formed, respectively, at predetermined distances from the trunk opening 8 and the leg openings 7.

1-2-4. Fiber Orientation

In the joint regions 9L and 9R, parts of fibers composing the chassis 2 are orientated so as to connect the first joint regions 91L and 91R to the second joint regions 92L and 92R, respectively. Specifically, parts of fibers composing the chassis 2 are arranged so as to stretch over both the first joint regions 91L and 91R and the second joint regions 92L and 92R, to consequently connect the first joint portions 94 and the second joint portions 95 in close proximity to each other. This is preferable because such an orientation of the fibers can inhibit a region between the first joint portions and the second joint portions from being continuously broken in the longitudinal direction (a so-called such straight cut). Furthermore, this is preferable because such an orientation of the fibers as to connect the first joint portions 94 and the second joint portions 95 that are adjacent to each other causes the first joint portions 94 and the second joint portions 95 to cooperate with each other to counter a force to peel the joint regions 9L and 9R. That is, this is preferable because a joining strength between the joint regions 9L and 9R is improved. Specifically, a joining strength in a case where the joint regions 9L and 9R are pulled to be peeled becomes greater, as compared with that in a case where the fibers are orientated in the longitudinal direction LD. Furthermore, the chassis 2 in the present embodiment includes stretchable fibers. Therefore, the joining strength in the case where the joint regions 9L and 9R are pulled to be peeled further becomes greater.

1-2-5. Joined State

A description is now provided of the change in a joined state in the joint regions 9L and 9R in a case where a force to peel the joint regions 9L and 9R is applied to the disposable diaper 1. When the force to peel the joint regions 9L and 9R is applied to the disposable diaper 1, an end, inside in the width direction WD and on the side of the body, of each of the first joint portions 94 is peeled. The joining is released with the non-woven fabric being broken at a peripheral edge of the first joint portion 94 by further applying the force so as to peel the joint regions 9L and 9R. Here, there is a non-joint portion having a predetermined length (a first distance) between the first joint portions 94 in the longitudinal direction LD. Even if nearly all of the first joint portions 94 in the first joint region 91L or 91R are released, the front trunk-surrounding region and the rear trunk-surrounding region are, therefore, not peeled from each other. Even if the first distance between the first joint portions 94 is short and the first joint portions 94 are densely formed, either the front trunk-surrounding region or the rear trunk-surrounding region may, in some cases, be broken in the process of releasing the joint portions.

Here, since the respective distances between the first joint regions 91L and 91R and the second joint regions 92L and 92R are more than 0 mm, and the fibers are oriented so as to connect the first joint portions 94 and the second joint portions 95, a so-called straight cut is inhibited.

Furthermore, since the respective distances between the first joint regions 91L and 91R and the second joint regions 92L and 92R are not more than 1.5 mm, and the fibers are oriented so as to connect the first joint portions 94 and the second joint portions 95, the first joint portions 94 and the second joint portions 95 cooperate with each other to counter a force to peel the joint regions 9L and 9R, resulting in an improved joining strength therebetween. That is, even with joining released in the vicinity of an end, on the side of the first joint portion 94, of the second joint portion 95, the fibers are not broken at an end, on the side of the second joint portion 95, of the first joint portion 94 so that the joined state is maintained. Therefore, durability of both the joint portions are combined with each other to develop a high joining strength.

1-2-6. Others

In the present embodiment, the disposable diaper 1 is inhibited from being broken in joint regions by joining laminates at outer edges in the width direction WD of the chassis 2. Therefore, a non-woven fabric having a low basis weight can be used for the chassis 2. Similarly, a non-woven fabric having a low breaking strength but being soft and having a good texture can be used for the chassis 2. This allows an added value in the disposable diaper 1 to be improved. Furthermore, non-woven fabrics respectively composed of materials that are not so compatible in joining can be used for the chassis 2. This further widens the scope of the selection of material for the non-woven fabric composing the chassis 2 and further widens the possibility of improving the added value.

Here, although in the present embodiment a side edge of the front trunk-surrounding region and a side edge of the rear trunk-surrounding region in the chassis 2 are arranged so as to be directed outward in the width direction WD to form the laminates, the present invention is not limited to the same. For example, they may be arranged such that one of them is directed outward in the width direction WD and the other is directed inward in the width direction WD.

What is claimed is:

1. An absorbent article comprising non-woven fabric composing a chassis having at least a front trunk-surrounding region and a rear trunk-surrounding region arranged therein, and having a width direction and a longitudinal direction perpendicular to the width direction, and a joined region where the front trunk-surrounding region and the rear trunk-surrounding region are joined to each other along both side edges thereof, the joined region comprising:
    at least a first joint region close to the inside of the chassis;
    a second joint region closer to an outside of the chassis than the first joint region; and
    a third joint region closer to the outside of the chassis than the second joint region,
    a plurality of first joint portions continuously formed in the longitudinal direction in the first joint region,
    a plurality of second joint portions continuously formed in the longitudinal direction in the second joint region,
    a plurality of third joint portions continuously formed in the longitudinal direction in the third joint region,
    each of the first joint portions and the second joint portions being formed to extend a greater distance in the width direction of the chassis than in the longitudinal direction of the chassis, and;
    the second joint portions including a plurality of end-side second joint portions disposed at an end side in the longitudinal direction of the second joint region and a plurality of center-side second joint portions disposed at a center portion in the longitudinal direction of the second joint region, the end-side second joint portions having greater areas than those of the center-side second joint portions,
    wherein the sum of the areas of the plurality of first joint portions in the first joint region is less than the sum of the areas of the second joint portions in the second joint region,
    wherein the sum of the areas of the plurality of third joint portions in the third joint region is less than the sum of the areas of the second joint portions in the second joint region, and
    wherein fibers composing the non-woven fabric in the first and second joint regions are oriented so as to stretch in the width direction of the chassis over both the first joint regions and the second joint regions to connect at least the first joint portion and the second joint portion in close proximity to each other.

2. The absorbent article according to claim 1, wherein the distance between respective arrays in the width direction of the first joint portions and the second joint portions is in the range of zero to 1.5 mm.

3. The absorbent article according to claim 1, wherein a first distance in a predetermined direction between the adjacent first joint portions of the plurality of first joint portions is greater than a second distance in the predetermined direction between the adjacent second joint portions of the plurality of second joint portions.

* * * * *